(12) United States Patent
Arstad et al.

(10) Patent No.: US 8,629,299 B2
(45) Date of Patent: Jan. 14, 2014

(54) RADIOFLUORINATED COMPOUNDS AND THEIR PREPARATION

(71) Applicant: Hammersmith Imanet Limited, London (GB)

(72) Inventors: Erik Arstad, London (GB); Matthias Eberhard Glaser, Amersham (GB)

(73) Assignee: Hammersmith Imanet Limited, London (GB)

( * ) Notice: Subject to any disclaimer, the term of this patent is extended or adjusted under 35 U.S.C. 154(b) by 0 days.

(21) Appl. No.: 13/898,131

(22) Filed: May 20, 2013

(65) Prior Publication Data
US 2013/0259802 A1 Oct. 3, 2013

Related U.S. Application Data

(62) Division of application No. 13/414,801, filed on Mar. 8, 2012, now Pat. No. 8,445,721, which is a division of application No. 12/297,347, filed on Oct. 16, 2008, now Pat. No. 8,148,575.

(30) Foreign Application Priority Data

Apr. 20, 2006 (NO) .................................... 20061759

(51) Int. Cl.
*C07C 337/00* (2006.01)
(52) U.S. Cl.
USPC .................. 564/29; 564/17; 564/26; 564/27; 564/28

(58) Field of Classification Search
None
See application file for complete search history.

(56) References Cited

U.S. PATENT DOCUMENTS

| 7,410,943 B2 * | 8/2008 | Cuthbertson et al. | ......... 514/1.1 |
| 8,148,575 B2 * | 4/2012 | Arstad et al. | .................... 564/29 |
| 8,445,721 B2 * | 5/2013 | Arstad et al. | .................... 564/29 |
| 2005/0070466 A1 * | 3/2005 | Cuthbertson et al. | .......... 514/10 |

FOREIGN PATENT DOCUMENTS

| WO | 03/006491 | 1/2003 |
| WO | 2005/012335 | 2/2005 |

OTHER PUBLICATIONS

Wuest, F., et.al. "Synthesis of 4-(18F-fluoromethyl)-2-chlorophenylisothio cyanate: A novel bifunctional 18F-labelling agent" Radiochimica ACTA, London, GB, vol. 92, 2004, pp. 349-353.

Cai, L. et.al. "Synthesis and evaluation of two 18F-labeled 6-iodo-2-(4'-N,N-dimethylamino)phenylimida zo[1,2a] pyridine derivatives as prospective radioligands for beta-amyloid in alzheimer's disease" Journal of Medicinal Chemistry, vol. 47, 2004, pp. 2208-2218.

Shiraishi, et.al. "Discovery of novel, potent, and selective small-molecule CCR5 antagonists as anti-HIV-1 agents: synthesis and biological evaluation of anilide derivatives with a quaternary ammonium moiety" J. Med. Chem, 2000, 43, pp. 2049-2063.

Poethko, et.al. "Two-step methodology for high-yield routine radiohalogenation of peptides: 18F-labeled RGD and octreotide analogs" Journal of Nuclear Medicine, vol. 45, No. 5 May 2004 pp. 892-902.

PCT/IB2007/001044 ISRWO Dated Nov. 2007.

* cited by examiner

*Primary Examiner* — Sudhakar Katakam

(57) ABSTRACT

The present invention provides a process for [$^{18}$F]-fluorination of biomolecules containing a primary amino group such as proteins and peptides and in particular of peptides. The invention further provides reagents for this process, in particular $^{18}$F-labelled prosthetic groups for use in the preparation as well as non-labelled intermediates useful in the preparation of the [$^{18}$F]-labelled prosthetic groups. [$^{18}$F]-labelled compounds useful as radiopharmaceuticals, specifically for use in Positron Emission Tomography (PET) are also provided.

3 Claims, No Drawings

RADIOFLUORINATED COMPOUNDS AND THEIR PREPARATION

This application is a divisional application of U.S. application Ser. No. 13/414,801 filed on Mar. 8, 2012, now allowed, which in turn is a divisional application of U.S. application Ser. No. 12/297,347 filed on Oct. 16, 2008, now U.S. Pat. No. 8,148,575, which is a filing under 35 U.S.C. 371 of international application number PCT/IB2007/001044, filed Apr. 20, 2007, which claims priority to application number 20061759 filed Apr. 20, 2006 in Norway, the entire disclosure of each of which is hereby incorporated by reference.

TECHNICAL FIELD OF THE INVENTION

The present invention relates to processes and reagents for [$^{18}$F]-fluorination, particularly of peptides. The resultant [$^{18}$F]-labelled compounds are useful as radiopharmaceuticals, specifically for use in Positron Emission Tomography (PET).

DESCRIPTION OF RELATED ART

Compounds labelled with short-lived positron emitting radionuclides are used for in vivo studies of human and non-human physiology. In particular, radiolabelled bioactive compounds which selectively interact with specific cell types are useful for the delivery of radioactivity to target tissues. The applications of bioactive compounds such as peptides and proteins, including antibodies and fragments of peptides are useful for receptor imaging. For example, radiolabelled peptides have significant potential for the delivery of radionuclides to the receptors expressed on cells of tissues, e.g. in tumours, infarcts and infected tissues for diagnosis, radiotherapy and monitoring of treatment. PET is a high resolution, non-invasive, imaging technique which has gained increased importance in the recent years for the visualisation of human disease.

In PET, $^{18}$F is one of the most widely used positron-emitting nuclides. $^{18}$F is relatively short-lived with a half-life ($t_{1/2}$) of 110 minutes and is hence a nuclide of choice for receptor imaging. However, one of the major disadvantages with [$^{18}$F]-labelling of compounds such as peptides and proteins is the laborious preparation which can only be achieved via prosthetic groups. Bio-molecules cannot be labelled directly with fluorine due to the harsh conditions involved. Strategies for preparing $^{18}$F-labelled biomolecules require methods where a [$^{18}$F]-labelled intermediate is prepared and coupled to the biomolecule, see e.g. WO 99/11590 and references therein.

It is of utmost importance that the preparation of the [$^{18}$F]-labelled intermediate and the coupling to the peptide or protein are fast and easy to perform and that they are amenable to kit formulations for use in the clinical setting. The yield of the preparation of the [$^{18}$F]-labelled intermediates ([$^{18}$F]-labelled prosthetic groups) as well as the coupling of the intermediate to the peptide or protein should be high enough so that multiple purifications can be avoided.

Methods for the labelling of biomolecules containing a primary amine group such as proteins and peptides with [$^{18}$F]-labelled prosthetic groups are continuously sought. Wüst, F., Müller, M. and Bergmann, R. in "Synthesis of 4-([$^{18}$F]fluoromethyl)-2-chlorophenylisothiocyanate: A novel bifunctional $^{18}$F-labelling agent" Radiochim. Acta 92 (2004) 349-353, describe a single step synthesis of the $^{18}$F-labelled prosthetic group of the title and also its conjugation with primary amines. The authors however reports that defluorination of the model compounds occurred in animal studies.

Therefore, there still exists a need for [$^{18}$F]-labelled prosthetic groups and methods which allow rapid introduction of the labelled group into biomolecules such as peptides and proteins to give [$^{18}$F]-labelled compounds in high radiochemical yield and purity. Additionally, there is a need for methods which are amenable to fascilitate preparations of radiopharmaceuticals in the clinical setting.

SUMMARY OF THE INVENTION

The present invention provides a process for [$^{18}$F]-fluorination of biomolecules containing a primary amine group such as proteins and peptides. The invention further provides reagents for this process, in particular [$^{18}$F]-labelled prosthetic groups for use in the preparation as well as non-labelled intermediates useful in the preparation of the [$^{18}$F]-labelled prosthetic groups. [$^{18}$F]-labelled compounds useful as radiopharmaceuticals, specifically for use in Positron Emission Tomography (PET) are also provided.

DETAILED DESCRIPTION OF THE INVENTION

The new process and intermediates prepared and used therein; and the compounds of the invention, their use as radiopharmaceutical imaging agents, their formulation and kits containing them are specified in the attached claims and in the specification hereinafter.

In one embodiment the invention comprises a process for preparing radiofluorinated biomolecules of formula (7)

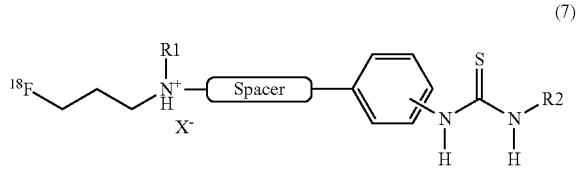

(7)

wherein
$R^1$ denotes H or $C_1$-$C_4$ alkyl where methyl is preferred,
Spacer denotes a $C_1$-$C_4$ alkylene group, optionally interrupted by a oxygen atom and where ethylene is a preferred Spacer,
or $R^1$ and Spacer together with the adjacent nitrogen atom form 4-azonia-spiro[3.5]nonyl or 4-aza-4-azonia-spiro[3.5]nonyl groups,
$R^2$ denotes a bio-molecule residue having at least one free amino function, preferably a peptide or protein residue,
and
X denotes a physiological acceptable anion, preferably a $C_1$-$C_4$ alkanesulphonate anion, e.g. the methanesulphonate anion,
comprising
a) reacting a compound of formula (5)

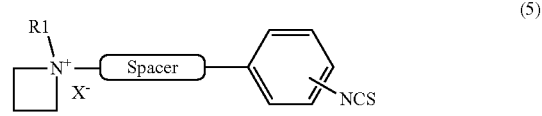

(5)

wherein $R^1$ and Spacer have the meanings above with a [$^{18}$F]-fluoride, and b) reacting the resulting labelled compound of formula (6)

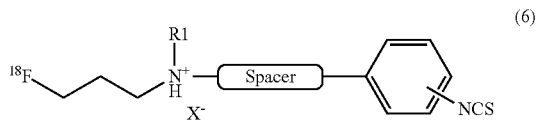

wherein $R^1$ and Spacer have the meanings above
with a peptide of formula (8)

$R^2NH_2$ (8)

wherein $R^2$ is as defined above,
to obtain the labelled [$^{18}$F]-fluorinated bio-molecule of formula (7).

The radiofluorination method of step a), useful to prepare the labelling reagent (6), can be carried out by standard methods e.g. in acetonitrile with [$^{18}$F]-KF-Kryptofix at a temperature below 80° C. e.g. by using microwave heating.

After the isolation of compound (6) by cation exchange solid phase extraction, compound (6) is incubated with a compound of formula $R^2NH_2$ (formula 8) in step b) wherein $R^2$ is a biomolecule residue to obtain a compound of formula (7).

Isothiocyanates are an established functionality to prepare stable bioconjugates. For examples see: Mao, S.-Y., editor: Walker, John M. "Conjugation of fluorochromes to antibodies" in Protein Protocols Handbook (2$^{nd}$ Edition), (2002), 351-354, publisher: Umana Press Inc. and Totowa, N. J; Jones, N.-., Dive, C. "Cell sensitivity assays: Detection of apoptotic cells in vitro using the TUNEL assay" Methods in Molecular Medicine 28 (1999) 31-38.

The compounds of formula (8) may contain any bio-molecule having a free primary amino group. Hence, $R^2$ designates the residue of a bio-molecule having a free amino function, e.g. a protein or a peptide having a free amino function at the N-terminal end and/or in the amino acid residue. Preferred such amino acids are lysine, hydroxylysine and arginine. Suitable groups $R^2$ comprise proteins, hormones, oligonucleotides, polyclonal and monoclonal antibodies and antibody fragments and peptide mimetics that are useful as targeting vectors.

The present process is particularly attractive for preparing relatively big peptides where there is no modification and/or control of the labelling site. The [$^{18}$F]-labelling reagent will bind to any available amino function on a peptide such as lysines or to the N-terminus amino acid.

Peptide residues comprising somatostatin analogues, such as octreotide, bombesine, vasoactive intestinal peptide, chemotactic peptide analogues, α-melanocyte stimulating hormone, neurotensin, Arg-Gly-Asp peptide and its analogues, human pro-insulin connecting peptide, insulin, endothelin, angiotensin, formyl, norleucyl-phenylalanyl-norleucyl-tyrosyl-lysine and annexin V are useful classes of biomolecules in the context of the invention. A further class of peptides for labelling are peptides containing the Arg-Gly-Asp sequence and its analogues, such as those described in WO 01/77145 and WO 03/006491. In one particular aspect, the compound $R^2NH_2$ is of formula (A)

Formula (A)

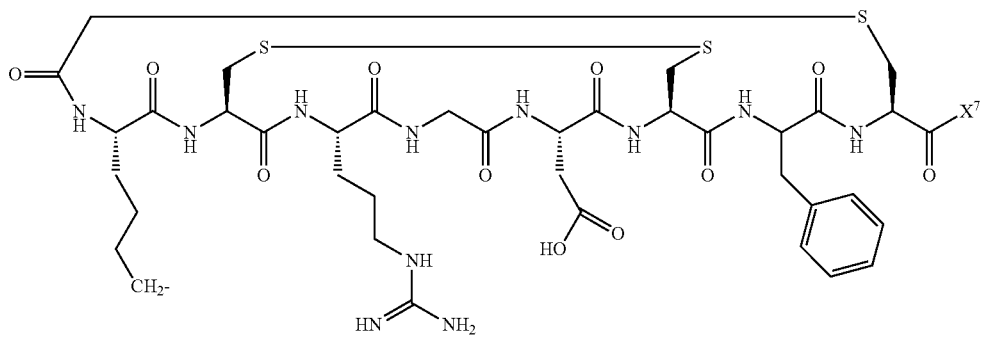

wherein $X^7$ has the meaning of

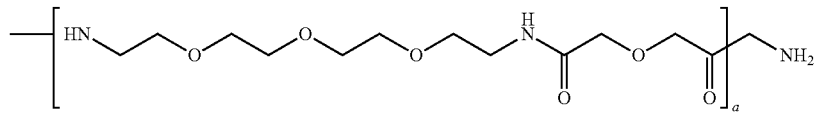

wherein a is an integer of from 1 to 10, preferably a is 1.

The [$^{18}$F]-labelled compounds of formula (7) wherein $R^2$ are as described above, are novel compounds that are useful as radiopharmaceuticals for use in PET imaging and represent another embodiment of the present invention. The radiotracers or formula (7) are sufficiently stable at physiological pH to allow use as in vivo diagnostic agents. The stability of the [$^{18}$F]-fluoropropyl group has been verified in a number of examples in vivo, see for instance: Cai, L., Chin, F. T., Pike, V. W., Toyama, H. Liow, J.-S., Zoghbi, S. S. et al. in "Synthesis and Evaluation of Two $^{18}$F-Labeled 6-Iodo-2-(4'-N,N-dimethylamino)phenylimidazo[1,2-a]pyridine Derivatives as Prospective Radioligands for Amyloid in Alzheimer's Disease" J. Med. Chem. 47 (2004) 2208-2218 and Maeda, M. Sasaki, S., Fukumura, T. et al. in "Positron-Emitting N-[$^{18}$F] Fluoroalkyl and [$^{18}$F]Fluoropyrrolidinyl Analogues of Eticloprode as potential in Vivo Radioligands for Dopamine $D_2$ Receptors" Chem. Pharm. Bull 40 (1992) 1793-1798.

Hence, compounds of formula (7) comprise a further embodiment of the invention.

The [$^{18}$F]-labelled compounds of formula (6) are novel compounds useful as intermediates for the preparation of radiopharmaceuticals for use in PET imaging and form a further embodiment of the present invention.

The compounds of formula (5) are also novel compounds useful as intermediates in the preparation of [$^{18}$F]-labelled prosthetic groups and form a still further embodiment of the present invention. The non-radioactive compound of formula (5) may form part of a radiofluorination kit for the preparation of compounds (6) and (7).

The process further comprises preparing the intermediate compounds of formula (2), formula (3), formula (4) and of formula (5).

c) The compound of formula (2)

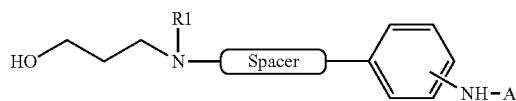

(2)

wherein
A denotes an amino protection group, e.g. BOC (tert-butyl ester), and
Spacer and R$^1$ have the meanings above
is prepared from a halide of formula (1)

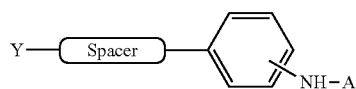

(1)

wherein
Y denotes a halogen atom, e.g. a bromine atom, and
Spacer and A have the meanings above
by reaction with a compound of formula (9)

R$^1$—NH—CH$_2$—CH$_2$—CH$_2$—OH    (9)

Compounds of formula (1) are commercially available.
The compound of formula (1) is reacted with a compound of formula (9), e.g. with 3-aminomethylpropan-1-ol in the presence of potassium carbonate and potassium iodide to give an aminoalcohol of formula (2), following the reaction procedure described by Kung, P.-P., Bharadwaj, R., Fraser, A. S., Cook, D. R., Kawasaki, A. M., and Cook, P. in "Solution-Phase Synthesis of Novel Linear Oxyamine Combinatorial Libraries with Antibacterial Activity", J. Org. Chem. 63 (1998), 1846-1852).

d) The aniline compounds of formula (3)

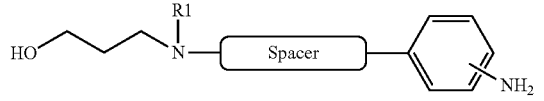

(3)

wherein R$^1$ and Spacer have the meanings above, is prepared from the compound of formula (2) by removal of the protecting group A such as the BOC group, e.g. by using trifluoroacetic acid.

e) The isothiocyanate compounds of formula (4)

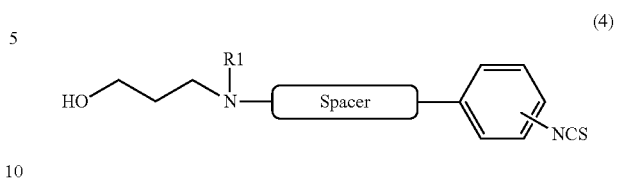

(4)

wherein R$^1$ and Spacer have the meanings above, are prepared by treatment of the compound of formula (3) with thiophosgene as outlined for an analogous compound by Wüst, F., Müller, M. and Bergman, R., in "Synthesis of 4-([$^{18}$F]-fluoromethyl)-2-chlorophenylisothiocyanate: A novel bifunctional $^{18}$F-labelling agent." Radiochim. Acta 92 (2004), 349-353.

f) The isothiocyanates of formula (4) are converted into the azetidinium salts, such as an azetidium methansulphonate, containing an isothiocyanate function of formula (5)

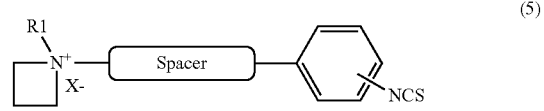

(5)

wherein R$^1$ and Spacer have the meanings above,

The preparation of the azetidinium salts containing the isothiocyanate function can be performed according to the procedure described by Kiesewetter, D. O. and Eckelman, W. C. "Utility of azetidium methanesulfonates for radiosynthesis of 3-[$^{18}$F]-fluoropropyl amines" in J. Label. Compd. Radiopharm. 47 (2004) 953-969 for the corresponding 7-[(4-cyanophenoxy)methyl]-4-azoniaspiro[3.5]nonane methanesulphonate.

The preparation is further illustrated in Scheme 1 wherein in the general formulas (1) to (7) the substituents have the following meanings:

R$^1$ denotes a methyl group

R$^2$ denotes R

A denotes BOC

Y denotes Bromine

Spacer denotes ethylene

Scheme 1

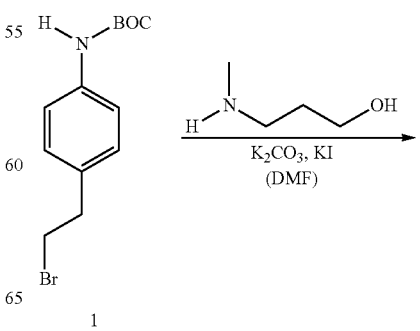

1

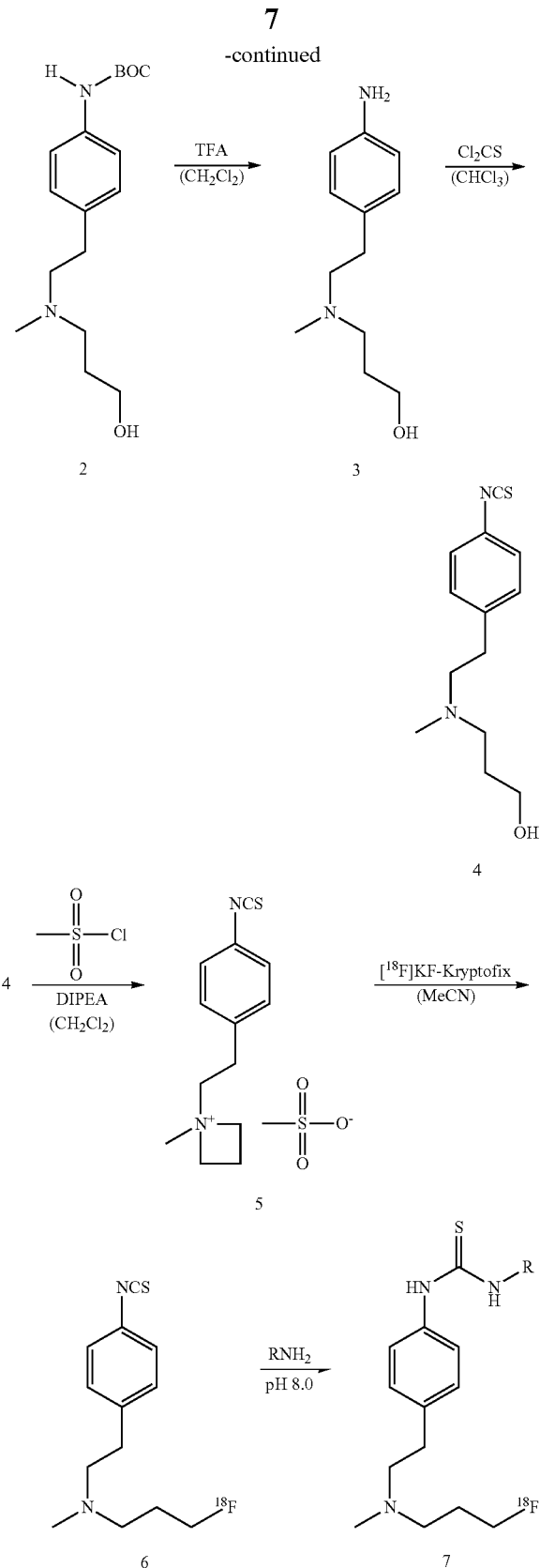

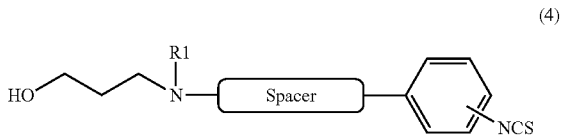

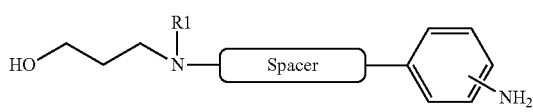

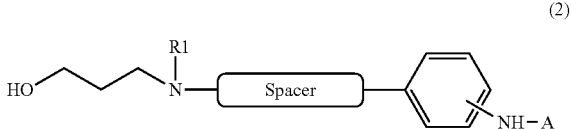

The $^{18}$F-labelled compounds of formula (7) are useful as radiopharmaceutical imaging agents, specifically as imaging agents for use in Positron Emission Tomography (PET). For use as imaging agents the compounds of formula (7) are preferably formulated as imaging agent compositions with solvents and/or excipients known from the state of art.

In a still further embodiment the invention comprises novel chemical compounds that are useful e.g. as intermediates in the process specified above and being of the formulas (2), (3) and (4):

wherein $R^1$ and Spacer have the meanings specified above wherein $R^1$ has the meanings specified above and Spacer denotes a $C_2$-$C_4$ alkylene group, optionally interrupted by a oxygen atom, or $R^1$ and Spacer together with the adjacent nitrogen atom form 4-azonia-spiro[3.5]nonyl or 4-aza-4-azonia-spiro[3.5]nonyl groups, wherein $R^1$ has the meanings above, Spacer denotes a $C_2$-$C_4$ alkylene group, optionally interrupted by a oxygen atom or $R^1$ and Spacer together with the adjacent nitrogen atom form 4-azonia-spiro[3.5]nonyl or 4-aza-4-azonia-spiro[3.5]nonyl groups, and A denotes an amino protection group such as BOC (tert-butyl ester).

In a method of diagnosis, compounds of formula (7) preferably provided as compositions as devised above, are administered to a human or animal body. Alternatively, the human or animal body is pre-administered with the compound of formula (7) prior to the commencement of the method of diagnosis. The body is examined with a diagnostic device and data are compiled from the examination. In an additional step the data may be are analysed to reach to a diagnosis. Preferably the compounds of formula (7) are used in PET imaging, where the diagnostic device is a Positron Emission Tomography scanner.

The invention further comprises a radiofluorination kit comprising a compound of formula (5) for the preparation of compounds of formulas (6) and (7). The radiofluorination kit may further comprise a compound of formula (8) and necessary additional reagents for the preparation of the imaging agent of formula (7).

EXAMPLES

Example 1

Preparation of compound (2)—(4-{2-[(3-Hydroxy-propyl)-methyl-amino]-ethyl}-phenyl)-carbamic acid tert-butyl ester (Step c)

One equivalent of compound (1), 0.5 equivalents of potassium carbonate, and 0.01 equivalents of potassium iodide are added sequentially to a solution of 3-methylaminopropan-1-ol (one equivalent) in DMF. The resulting mixture is stirred at 65° C. for 12 h. The reaction mixture is evaporated in vacuo and partitioned between ethyl acetate and water. The combined organic layers are dried ($Na_2SO_4$), filtered, and evaporated to give a residue. Purification of the residue by flash column chromatography produces the compound of formula (2).

Example 2

Preparation of compound (3)—(3-{[2-(4-Amino-phenyl)-ethyl]-methyl-amino}-propan-1-ol (Step d)

Compound (2) is dissolved in dichloromethane and trifluoroacetic acid (10 equivalents) added with stirring. After stirring for two hours at room temperature, the solvent is removed in vacuo. The residue is dissolved in dichloromethane and washed with a 5% sodium bicarbonate solution, dryed with brine and magnesium(II) sulfate. Removal of the solvent affords compound (3).

Example 3

Compound (4)—3-{[2-(4-Isothiocyanato-phenyl)-ethyl]-methyl-amino}-propan-1-ol (Step e)

To a suspension of compound (3) with barium(II) carbonate (5 equivalents) in chloroform a solution of thiophosgene (one equivalent) in chloroform is added at 0° C. with stirring. After warming up to room temperature, stirring is continued for one hour. Water is added and the crude product extracted with chloroform. After drying with brine and magnesium(II) sulfate, the product is purified by flash chromatography (silica, ethyl acetate/50% n-hexane).

Example 4

Compound (5)—Methanesulfonate 1-[2-(4-isothio-cyanato-phenyl)-ethyl]-1-methyl-azetidinium (Step f)

A solution of compound (4) in chloroform is mixed with methanesulfonyl chloride (1.1 equivalents) and triisopropyl-ethylamine (4 equivalents) and stirred for one hour at room temperature. The intermediate mesylate is isolated by flash chromatography (silica, ethyl acetate/50% n-hexane) and subsequently refluxed in chloroform for 12 h. The solvent is removed in vacuo and the residue triturated with ethyl acetate to form compound (5) as a solid.

Example 5

Compound (6)—(3-[$^{18}$F]Fluoro-propyl)-[2-(4-isothiocyanato-phenyl)-ethyl]-methyl-amine (Step a)

To a Wheaton vial charged with Kryptofix® (10 mg), potassium carbonate (1 mg dissolved in 0.05 ml water), and acetonitrile (0.8 ml) the fluorine-18 containing water (10 mCi, 1 ml) is added. The solvent is removed by heating at 110° C. for 30 min under a stream of nitrogen. Anhydrous acetonitrile (0.5 ml) is added and again evaporated as before. This step is repeated twice. The vial is cooled to room temperature followed by injecting a solution of compound (5) (1 mg) in anhydrous acetonitrile (0.2 ml). The reaction mixture is heated at 80° C. for 5 min and quenched in 0.5 ml of water. Compound (6) is isolated by solid phase extraction from an SCX cartridge (washing with water and eluting product by using a solution of water/25 ethanol).

Example 6

Compound (7)—Radiolabelling Annexin-V with Compound (6) (Step b)

A solution of compound (6) is concentrated by a stream of nitrogen to 0.05 ml. A solution of annexin-V in borate buffer pH 8.0 (0.1 M) is prepared by dialysis and mixed with compound (6). After incubation for 30 min at room temperature, the $^{18}$F-labelled annexin-V (7) is purified using size exclusion chromatography.

What is claimed is:

1. A method of diagnosis comprising examining a human or animal body with a diagnostic device and compiling data from the examination, wherein the body is preadministrated with a compound of formula (7):

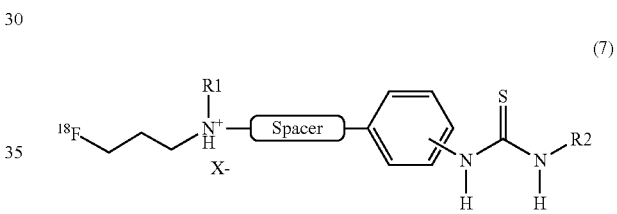

(7)

wherein $R^1$ denotes H or $C_1$-$C_4$ alkyl, Spacer denotes a $C_1$-$C_4$ alkylene group optionally interrupted by an oxygen atom, $R^2$ denotes a bio-molecule residue having at least one free amino function, and X denotes a physiological acceptable anion.

2. A method of diagnosis comprising administration of a compound of formula (7):

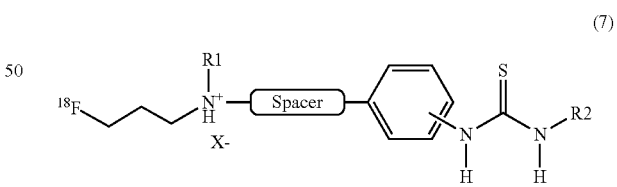

(7)

wherein $R^1$ denotes H or $C_1$-$C_4$ alkyl, Spacer denotes a $C_1$-$C_4$ alkylene group optionally interrupted by an oxygen atom, $R^2$ denotes a bio-molecule residue having at least one free amino function, and X denotes a physiological acceptable anion, to a human or animal body, examining the body with a diagnostic device and compiling data from the examination.

3. A method of claim 2 wherein the diagnostic device is a Positron Emission Tomography scanner.

* * * * *